US009107976B2

(12) United States Patent
Son et al.

(10) Patent No.: US 9,107,976 B2
(45) Date of Patent: Aug. 18, 2015

(54) BIO-ADHESIVE AGENT COMPRISING SURFACE-MODIFIED HYDROXYAPATITE AND USE THEREOF

(75) Inventors: Young Sook Son, Seoul (KR); Eun Ah Lee, Seoul (KR); Seung Woo Nam, Suwon-si (KR)

(73) Assignee: UNIVERSITY-INDUSTRY COOPERATION GROUP OF KYUNGHEE UNIVERSITY, Yongin-Si (KR)

( * ) Notice: Subject to any disclaimer, the term of this patent is extended or adjusted under 35 U.S.C. 154(b) by 209 days.

(21) Appl. No.: 13/702,852

(22) PCT Filed: Nov. 10, 2011

(86) PCT No.: PCT/KR2011/008529
§ 371 (c)(1),
(2), (4) Date: Dec. 7, 2012

(87) PCT Pub. No.: WO2012/067375
PCT Pub. Date: May 24, 2012

(65) Prior Publication Data
US 2013/0078291 A1    Mar. 28, 2013

(30) Foreign Application Priority Data

Nov. 17, 2010 (KR) .......................... 10-2010-0114232

(51) Int. Cl.
*A61L 24/00* (2006.01)
*A61L 24/02* (2006.01)
*A61L 27/32* (2006.01)

(52) U.S. Cl.
CPC ............... *A61L 24/00* (2013.01); *A61L 24/02* (2013.01); *A61L 27/32* (2013.01); *A61L 2400/18* (2013.01)

(58) Field of Classification Search
None
See application file for complete search history.

(56) References Cited

U.S. PATENT DOCUMENTS

| 5,279,831 A * | 1/1994 | Constantz et al. ............ 424/423 |
| 2010/0272693 A1* | 10/2010 | Lee et al. ..................... 424/93.7 |
| 2010/0286790 A1 | 11/2010 | Gruner et al. |

FOREIGN PATENT DOCUMENTS

| EP | 1 508 586 A1 | 2/2005 |
| WO | WO 2009/073068 A2 | 6/2009 |

OTHER PUBLICATIONS

WI Jaffe, DF Scott. "Current Concepts Review: Total Hip Arthroplasty with Hydroxyapatite-Coated Prostheses." The Journal of Bone and Joint Surgery, vol. 78-A No. 12, Dec. 1996, pp. 1918-1934.*
International Search Report issued in PCT/KR2011/008529 mailed May 17, 2012.

* cited by examiner

*Primary Examiner* — Isaac Shomer
(74) *Attorney, Agent, or Firm* — Birch, Stewart, Kolasch & Birch, LLP

(57) ABSTRACT

The present invention relates to a bio-adhesive agent comprising a surface-modified hydroxyapatite and its use. More specifically, the present invention relates to a bio-adhesive agent for the adhesion between bone and bone, bone and tissue, bone and cartilage, or bone and tendon, or for the adhesion of a shield between bones or of an artificial joint, which comprises a surface-modified hydroxyapatite as an active ingredient, wherein the surface-modified hydroxyapatite is characterized in that a certain linker compound is covalently bonded to the surface of the hydroxyapatite; a method for coating the surface of a metal prosthesis using the surface-modified hydroxyapatite; and a metal prosthesis coated with the surface-modified hydroxyapatite obtained by said method.

2 Claims, 5 Drawing Sheets

Confirmation of Attachment by Autologous Chondrocyte Transplantation Model in Rabbit

- Animal model: Rabbit
- Wound size: 5mm half-thickness
- Cell source: P2 XDSC sheet culture Cell clump      Cell clump+ HA-TPDA (3 weeks upon transplant)

Surface-modification of titanium prosthesis using HA-TPDA

BIO-ADHESIVE AGENT COMPRISING SURFACE-MODIFIED HYDROXYAPATITE AND USE THEREOF

TECHNICAL FIELD

The present invention relates to a bio-adhesive agent comprising a surface-modified hydroxyapatite and its use. More specifically, the present invention relates to a bio-adhesive agent for the adhesion between bone and bone, bone and tissue, bone and cartilage, or bone and tendon, or for the adhesion of a shield between the bones or of an artificial joint, which comprises a surface-modified hydroxyapatite as an active ingredient, wherein the surface-modified hydroxyapatite is characterized in that a certain linker compound is covalently bonded to the surface of the hydroxyapatite; a method for coating the surface of a metal prosthesis using the surface-modified hydroxyapatite; and a metal prosthesis coated with the surface-modified hydroxyapatite obtained by said method.

BACKGROUND ART

Tissue-engineering methods for the repair of damaged tissue include (i) forming a tissue from expanded and cultured cells, and transplanting said tissue, (ii) loading expanded and cultured cells at a scaffold and transplanting said scaffold, or (iii) transplanting a scaffold only without cells.

In the case of cartilage regeneration, expanded and cultured cells can be cultured in a chondrogenic medium to form cartilage which is transplanted into a damaged region of cartilage to induce regeneration of cartilage. This method has the advantage of being able to get a definitive therapeutic effect, compared with a method of injecting cells. However, in case the transplanted cartilage tissues do not integrate into the existing tissues, a full therapeutic effect cannot be expected.

This integration (connectivity) may be achieved by carrying out a suture, but in this case the subject tissues must have a structure that can be connected by a suture. It is impossible to apply a suture to a tissue having a structure that cannot be sutured. For example, a tissue that makes up cartilage or bone has limitations for having a suture applied thereon. In particular, when a connection between bone and cartilage is necessary as is in, for instance, the articular cartilage transplantation, it is not easy to carry out such a suture method and there is the shortcoming that a suture area has the potential to cause inflammation. Furthermore, in the case of widely occurring cartilage damage such as degenerative arthritis, it is not easy to find a way to achieve a connection of tissues over a large area.

In order to resolve these problems, a bio-adhesive agent in the form of a paste has been developed which exhibits an adhesive effect between cartilage and cartilage. However, this agent has a major disadvantage due to the fact that the applied adhesive materials formed insulation between the two attached cartilage tissues making it impossible to communicate or exchange the nutrient and/or growth factors and thus two different disconnected cartilage layers are formed bordering the attached surface. Moreover, the previously developed bio-adhesive agents are not effective in achieving a connection (adhesion) between bone and cartilage in the full-thickness wound.

Therefore, there is a need to develop a new bio-adhesive agent that is suitable for the desired tissue regeneration.

Hydroxyapatite is an inorganic substance that constitutes calcified tissues in vivo such as teeth and bone. Hydroxyapatite has the highest crystallinity among calcium phosphate compounds, so its speed of decomposition is accordingly slow, but it has high bio-compatibility as it is a substance comprising natural tissues in vivo. Hydroxyapatite is known to represent the most high bone regeneration effect among various kinds of bone substitutes.

In the previous study, the present inventors devised a method for coating a desired functional group on the surface of hydroxyapatite. Specifically, PCT Publication No. WO 2009/073068, which is an earlier application by the present inventors, disclosed an artificial bone sponge prepared by a process that comprises: modifying the surface of hydroxyapatite using an organic synthesis method so that a functional group such as aldehyde is revealed on the surface of hydroxyapatite; mixing the obtained surface-modified hydroxyapatite with an aqueous solution of chitosan for gellation; and lyophilizing the same. However, WO 2009/073068 teaches only the combination with a second ingredient such as chitosan and does not teach a use of the surface-modified hydroxyapatite alone.

The present inventors have performed continuous study on a use of the surface-modified hydroxyapatite alone without addition of a second ingredient such as chitosan. As a result, they discovered that the surface-modified hydroxyapatite exhibits a satisfactory adhesive strength between bone and cartilage, confirming its potential as a new bio-adhesive agent, and completed the present invention.

DISCLOSURE OF INVENTION

Technical Problem

Therefore, the object of the present invention is to provide a use of the surface-modified hydroxyapatite as a new bio-adhesive agent.

Solution to Problem

In order to solve the above technical problem, the present invention provides a bio-adhesive agent comprising a surface-modified hydroxyapatite as an active ingredient, wherein the surface-modified hydroxyapatite is characterized in that a linker compound selected from the group consisting of the following formulas (1) to (5) is covalently bonded to the surface of the hydroxyapatite:

$$R_3\text{Si-L-X} \quad (1);$$

$$R_3\text{Si-L-Y} \quad (2);$$

$$\text{Y-L-Y} \quad (3);$$

$$\text{Y—Y} \quad (4);$$

and $$R_3\text{Si-L} \quad (5),$$

wherein

R represents halogen, $C_{1-4}$alkoxy or $C_{1-4}$alkyl, provided that at least one of the three R groups is halogen or $C_{1-4}$alkoxy;

L represents substituted or unsubstituted $C_{1-17}$alkyl, $C_{1-17}$aralkyl, aryl, or heteroaryl comprising one or more heteroatoms selected from oxygen, nitrogen and sulfur;

X represents a leaving group selected from the group consisting of halogen, isocyanate (—NCO), tosyl and azide;

Y represents a reactive functional group of coordinate compounds capable of exchanging ligands, selected from the group consisting of hydroxyl, thiol, amine, ammonium, sulfone and its salts, carboxyl acid and its salts, acid anhydride, epoxy, aldehyde, ester, acrylate, isocyanate (—NCO), saccharide residue, double bond, triple bond, diene, diyne, alkylphosphine and alkyl arsine, wherein said reactive functional group may be located at the center of the linker compound as well as at both ends of the linker compound.

The present invention also provides a method for coating the surface of a metal prosthesis using the surface-modified hydroxyapatite; and a metal prosthesis coated with the surface-modified hydroxyapatite obtained by said method.

Advantageous Effects of Invention

Differently from the previous bio-adhesive agents, the bio-adhesive agent comprising the surface-modified hydroxyapatite as an active ingredient according to the present invention can achieve an adhesive effect with full integration such that disconnection between tissues to be adhered does not occur.

In addition, since the active ingredient hydroxyapatite itself is capable of osteogenesis, when the bio-adhesive agent of the present invention is applied between bone and cartilage or bone and tissue, it can promote regeneration of bone locally at the site to which cartilage or tissue is attached. Thus, it is expected that the bio-adhesive agent of the present invention would exhibit an excellent adhesive effect between bone and cartilage or bone and tissue.

Furthermore, if the surface of a prosthesis made by metal such as titanium is coated with the bio-adhesive agent of the present invention, the surface-modified hydroxyapatite is attached to the surface of the metal prosthesis and this is expected to resolve the problem of integration with natural tissues, which is a drawback in using the previous metal prosthesis.

MODE FOR THE INVENTION

Figure 1:
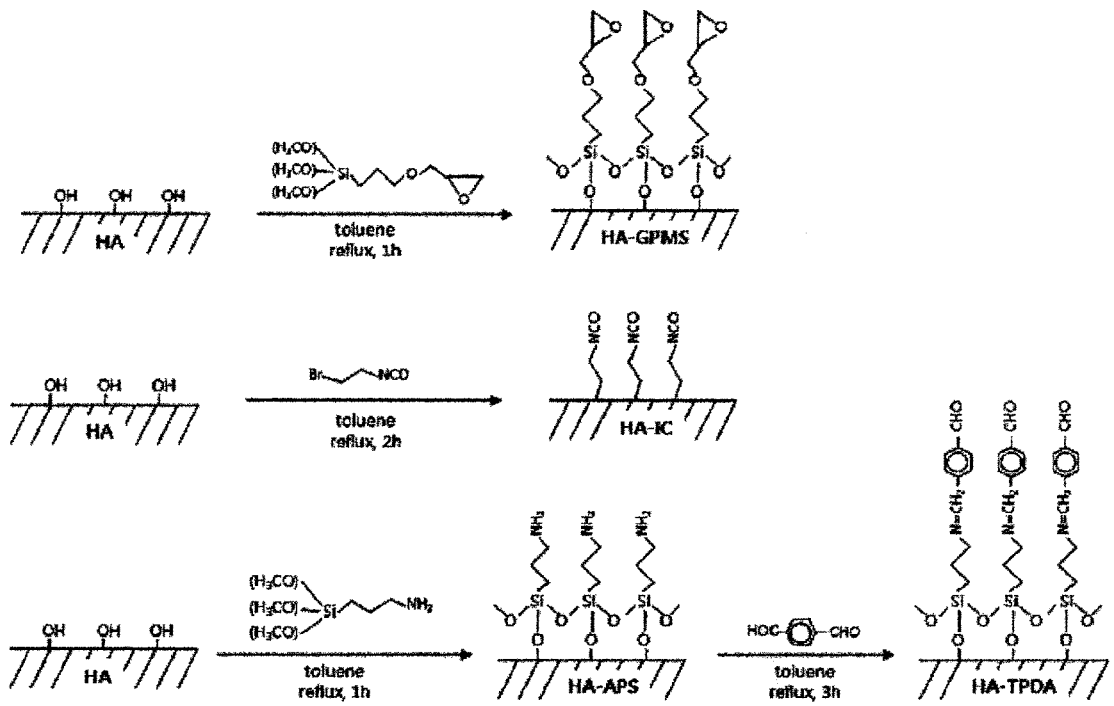
FIG. 1 is a schematic view showing a process for preparing the surface-modified hydroxyapatite (HA). The first one is a synthesis process of HA-GPMS (glycidyloxypropyl trimethoxysilane), the second one is a synthesis process of HA-EI (ethylisocyanate), and the third one is a synthesis process of HA-APS (aminopropyltriethoxysilane)-TPDA (terephthaldicarboxaldehyde).

The first aspect of the present invention relates to a bio-adhesive agent comprising a surface-modified hydroxyapatite as an active ingredient, wherein the surface-modified hydroxyapatite is characterized in that a linker compound selected from the group consisting of the following formulas (1) to (5) is covalently bonded to the surface of the hydroxyapatite:

(1);

(2);

(3);

(4);

and

(5), wherein

R represents halogen, $C_{1-4}$alkoxy or $C_{1-4}$alkyl, provided that at least one of the three R groups is halogen or $C_{1-4}$alkoxy;

L represents substituted or unsubstituted $C_{1-17}$alkyl, $C_{1-17}$aralkyl, aryl, or heteroaryl comprising one or more heteroatoms selected from oxygen, nitrogen and sulfur;

X represents a leaving group selected from the group consisting of halogen, isocyanate (—NCO), tosyl and azide;

Y represents a reactive functional group of coordinate compounds capable of exchanging ligands, selected from the group consisting of hydroxyl, thiol, amine, ammonium, sulfone and its salts, carboxyl acid and its salts, acid anhydride, epoxy, aldehyde, ester, acrylate, isocyanate (—NCO), saccharide residue, double bond, triple bond, diene, diyne, alkylphosphine and alkyl arsine, wherein said reactive functional group may be located at the center of the linker compound as well as at both ends of the linker compound.

In the definition of L, a substituent on $C_{1-17}$alkyl, $C_{1-17}$aralkyl, aryl or heteroaryl moiety is preferably one or more selected from the group consisting of hydroxyl, $C_{1-6}$ alkyl, $C_{1-6}$alkoxy, halogen, nitro, amino, cyano, halo$C_{1-6}$ alkyl, $C_{1-6}$alkylamino, di$C_{1-6}$ alkylamino, acyl and acyloxy.

The term "aryl" includes optionally substituted phenyl or naphthyl.

The term "heteroaryl" includes 5- or 6-membered monocyclic heteroaryl, or 9- or 12-membered bicyclic heteroaryl, which may contain 1, 2 or 3 heteroatom(s) selected from oxygen, nitrogen and sulfur. Non-limiting examples of heteroaryl include thienyl, furanyl, pyrrolyl, imidazolyl, oxazolyl, thiazolyl, benzothienyl, benzofuranyl, benzimidazolyl, benzoxazolyl, benzothiazolyl and the like.

The term "acyl" refers to a carbonyl moiety attached to a hydrogen atom (i.e., formyl group), an optionally substituted alkyl or alkenyl chain, or heterocycle.

WO 2009/073068 disclosed exemplary methods for modifying the surface of hydroxyapatite. However, WO 2009/073068 teaches only the use of an artificial bone sponge prepared by mixing the surface-modified hydroxyapatite with an aqueous solution of chitosan for gellation and lyophilizing the same, and does not teach a use of the surface-modified hydroxyapatite alone as a bio-adhesive agent.

In addition, WO 2009/073068 states that the linker compound must be covalently bonded to the hydroxyapatite only via the —O—Si— moiety or an isocyanate moiety. However, the active ingredient of the present invention, the surface-modified hydroxyapatite, does not require that the linker compound be covalently bonded to the hydroxyapatite necessarily via the —O—Si— moiety or an isocyanate moiety. For the surface-modified hydroxyapatite of the present invention, it is sufficient as long as the linker compound selected from the group consisting of the above formulas (1) to (5) is covalently bonded to the surface.

Herein, unless otherwise defined, the term "linker compound" refers to one or more compounds selected from the group consisting of the above formulas (1) to (5).

A great variety of linker compounds can be applied through the use of hydroxyl groups on the surface of hydroxyapatites. Representative examples thereof include glycidyloxypropyl trimethoxysilane (GPMS), ethylisocyanate (EI) or aminopropyltriethoxysilane (APS)-terephthaldicarboxaldehyde (TPDA), as shown in FIG. 1.

Among the methods for modifying the surface of hydroxyapatites disclosed in WO 2009/073068, a method for preparing hydroxyapatite-terephthaldicarboxaldehyde (HA-TPDA) is as follows. After calcination of HA, HA is reacted with APS (57.3 mM, 100 ml) under an argon atmosphere at 110° C. for 1 hour. The thus-obtained HA bonded by APS is washed several times in the order of toluene, ethanol and methanol, and dried to provide HA-APS.

Next, HA-APS is dispersed in toluene and then slowly added in strongly stirred TPDA (3 g) dissolved in toluene using a micropipette. The thus-obtained mixture is refluxed under an argon atmosphere at 120° C. for 2 hours to provide hydroxyapatite whose surface is bonded by APS-TPDA, which is called "HA-TPDA." The obtained HA-TPDA is washed several times in the order of toluene, ethanol and methanol, and vacuum-dried to provide HA-TPDA powders.

In one embodiment, the surface-modified hydroxyapatites of the present invention are characterized in that the end of the bonded linker compounds has a functional group selected from carbonyl, carboxyl and epoxy, and such functional groups will react with amine groups present in tissues such as bone, tissue, cartilage and tendon.

In the present invention, a hydroxyapatite as an ingredient of the surface-modified hydroxyapatite can be selected from the group consisting of the following i) to x):

i) natural and synthesized hydroxyapatite;

ii) biological apatite derived from bone or teeth;

iii) apatite of the formula $M_{10}(ZO_4)_6X_2$ wherein M is selected from the group consisting of $Ca^{2+}$, $Cd^{2+}$, $Sr^{2+}$, $Ba^{2+}$, $Pb^{2+}$, $Zn^{2+}$, $Mg^{2+}$, $Mn^{2+}$, $Fe^{2+}$, $Ra^{2+}$, $H^+$, $HaO^+$, $Na^+$, $K^+$, $Al^{3+}$, $Y^{3+}$, $Ce^{3+}$, $Nd^{3+}$, $La^{3+}$ and $C^{4+}$;

iv) apatite of the formula $M_{10}(ZO_4)_6X_2$ wherein Z is selected from the group consisting of $PO_4^{3-}$, $CO_3^{3-}$, $CrO_4^{3-}$, $AsO_4^{3-}$, $VO_4^{3-}$, $UO_4^{2+}$, $SO_4^{3-}$, $SiO_4^{4-}$ and $GeO_4^{4-}$;

v) apatite of the formula $M_{10}(ZO_4)_6X_2$ wherein X is selected from the group consisting of $OH^-$, $OD^-$, $F^-$, $Cl^-$, $Br^-$, $BO^{2-}$, $CO_3^{2-}$ and $O^{2-}$;

vi) natural and synthesized hydroxyapatite of the above item i) in the form of a powder, granule, thin film, porous molecule, dense molecule, rod or plate;

vii) biological apatite of the above item ii) in the form of a powder, granule, thin film, porous molecule, dense molecule, rod or plate;

viii) apatite in sol or gel phase obtained by dispersing the natural and synthesized hydroxyapatite of the above item i) or vi) in an aqueous solution;

ix) a substance selected from the group consisting of monocalcium phosphate monohydrate ($Ca(H_2PO_4)_2.H_2O$), calcium metaphosphate ($Ca(PO_3)_2$), dicalcium phosphate dehydrate ($CaHPO_4.H_2O$), tricalcium phosphate ($Ca_3(PO_4)_2$), tetracalcium phosphate ($Ca_4P_2O_9$), octacalcium phosphate ($Ca_8H_2(PO_4)_6$) and amorphous calcium phosphate; and x) a mixture of hydroxyapatite and a substance selected from the group consisting of monocalcium phosphate monohydrate ($Ca(H_2PO_4)_2.H_2O$), calcium metaphosphate ($Ca(PO_3)_2$), dicalcium phosphate dehydrate ($CaHPO_4.H_2O$), tricalcium phosphate ($Ca_3(PO_4)_2$), tetracalcium phosphate ($Ca_4P_2O_9$), octacalcium phosphate ($Ca_8H_2(PO_4)_6$) and amorphous calcium phosphate.

As described above, hydroxyapatites can be in the form of a powder, granule, thin film, porous molecule, dense molecule, rod or plate, and are preferably used in the form of a powder. Differently from the previous bio-adhesive agents in the form of a paste, the bio-adhesive agents of the present invention in the form of a powder are more preferable in achieving an adhesive effect with full integration such that disconnection does not occur between tissues to be adhered.

Specifically, the present inventors bonded the linker compounds to the surface of hydroxyapatite crystal powders and confirmed that functional groups existing at the end of the linker compounds can form a covalent bond with amine groups under an aqueous atmosphere. In addition, via ninhydrin reaction the present inventors verified the existence of amine groups on the surface of the subject tissues such as bone, cartilage and tendon, and thus confirmed that hydroxyapatites with aldehyde groups on their surface are capable of binding with these tissues.

In addition, the present inventors attached multiple layers of cells in the form of a sheet onto the surface of cartilage using hydroxyapatites with aldehyde groups on their surface, and cultured the same. As a result, they confirmed that the form of the sheet was remained for a long time compared with that of a general hydroxyapatite-applied group. Furthermore, the present inventors attached clump-cultured bone marrow stromal cells (BMSCs) to a piece of ectopic bone which had been subcutaneously formed in a nude mouse, and confirmed that the cells exhibited an excellent adhesion.

Therefore, the bio-adhesive agent of the present invention may be useful in the adhesion between bone and implant. Specifically, the bio-adhesive agent of the present invention may be useful for the adhesion between bone and bone, bone and tissue, bone and cartilage, or bone and tendon, and may also be useful for the adhesion of a shield between bones or for the attachment of an artificial joint.

In addition, since the active ingredient hydroxyapatite itself is capable of osteogenesis, when the bio-adhesive agent of the present invention is applied between bone and cartilage or bone and tissue, it can promote regeneration of bone locally at the site to which cartilage or tissue is attached. Thus, it is expected that the bio-adhesive agent of the present invention would exhibit an excellent adhesive effect between bone and cartilage or bone and tissue.

Figure 10:
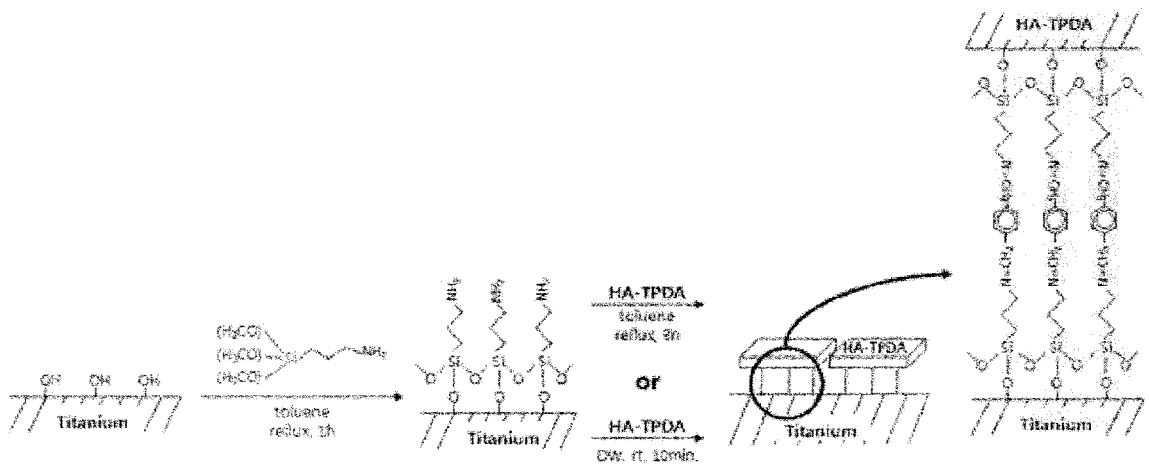
FIG. 10 is a schematic view showing a method for modifying the surface of a prosthesis comprising applying a linker compound on the surface of a titanium prosthesis and coupling it with HA-TPDA.

The second aspect of the present invention relates to a method for coating the surface of a metal prosthesis using the surface-modified hydroxyapatite. With reference to FIG. 10, the linker compounds are applied to the surface of a metal prosthesis, and the surface-modified hydroxyapatites (for example, HA-TPDA) are then coupled thereto so that the surface of the prosthesis is modified.

In one embodiment, the method for coating the surface of a metal prosthesis according to the present invention comprises a) interlinking APS to the surface of a titanium prosthesis, and b) applying HA-TPDA to combine with the above APS. As a result, the surface of the prosthesis is coated with HA-TPDA.

The third aspect of the present invention relates to a metal prosthesis coated with the surface-modified hydroxyapatites obtained by the above method. One end of the surface-modified hydroxyapatites is combined with the linker compounds (for example, APS) of the metal prosthesis, and functional groups existing in the other free end may react with amine groups existing in tissues such as bone, tissue, cartilage and tendon.

The metal prosthesis of the present invention may allow osteoblasts to generate bone on the surface of an implant because the surface-modified hydroxyapatites are attached to the surface of the prosthesis, and thus is expected to resolve the problem of integration with natural tissues, which is a drawback in using the previous metal prosthesis.

Hereinafter, the present invention will be described in more detail with reference to the following working examples. The working examples are provided only to help understanding of the invention but are not to be construed as limiting the scope of the invention.

EXAMPLES

Example 1

Surface Modification of Hydroxyapatites and Confirmation

Glycidyloxypropyl trimethoxysilane (GPMS) or aminopropyltriethoxysilane (APS)-terephthaldicarboxaldehyde (TPDA) was used as a silane-based linker compound, and ethylisocyanate (EI) was used as an isocyanate-based linker compound. These linker compounds and hydroxyapatite crystal powders were added to toluene and refluxed at 110° C. for 1 hour so that the linker compounds were attached to the surface of the hydroxyapatites via a silane or isocyanate group. This procedure is shown in FIG. 1. The first one is a synthesis process of HA-GPMS, the second one is a synthesis process of HA-EI, and the third one is a synthesis process of HA-TPDA.

Figure 2:
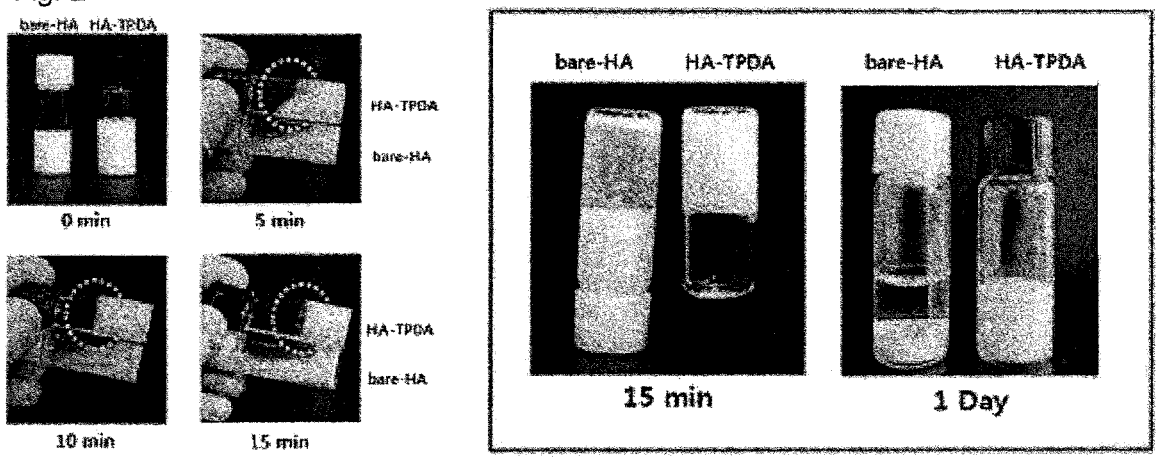
FIG. 2 is a picture showing a process of reaction with an aqueous solution of chitosan and the result, comparing the surface-modified hydroxyapatite (HA-TPDA) and a general hydroxyapatite (bare-HA), in order to confirm a coupling between an aldehyde group on the surface of the surface-modified hydroxyapatide and an amine group.

In order to confirm a coupling between aldehyde groups on the surface of the surface-modified hydroxyapatites and amine groups, HA-TPDA and general hydroxyapatites (bare-HA) were each mixed with an aqueous solution of chitosan. As a result, as shown in FIG. 2, in the case of HA-TPDA, chemical bonding started to take place before the end of 5 minutes, and after about 10 minutes it was observed that the mixed solution turned into a gel form that did not flow. In contrast, the general hydroxyapatites did not turn into a gel form. From the results, it was confirmed that a coupling between aldehyde groups on the surface of HA-TPDA and amine groups of chitosan took place.

Example 2

Confirmation of Presence of Amine Groups on the Surface of Natural Tissues

In order to achieve reaction with HA-TPDA, amine groups must be present on the surface of tissues to be attached. Whether or not amine groups are present on the surface of the subject tissues to be attached was determined as follows.

Figure 3:
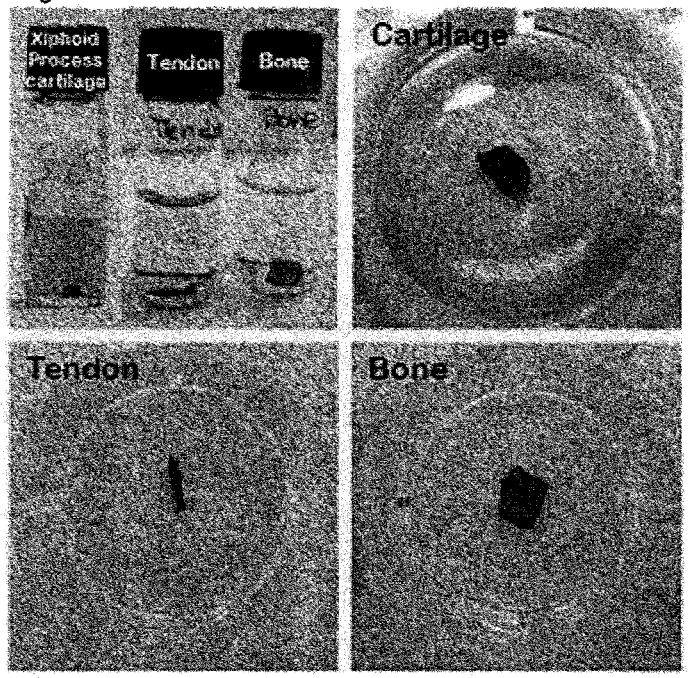
FIG. 3 is a picture confirming whether or not an amine group capable of reacting with HA-TPDA is present on the surface of the subject tissues to be attached to HA-TPDA via ninhydrin reaction.

Cartilage, bone and tendon tissues were carefully isolated from a mouse so that connective tissues were not included. As shown in FIG. 3, the isolated tissues were added to 6% ninhydrin in 98% ethanol, heated at 96° C. for 10 minutes and determined on whether or not the tissues exhibit color. As a result, it was confirmed that the cartilage, bone and tendon tissues have amine groups.

Example 3

In vitro Culture Experiment in Order to Confirm the Adhesive Ability of HA-TPDA

Figure 4:
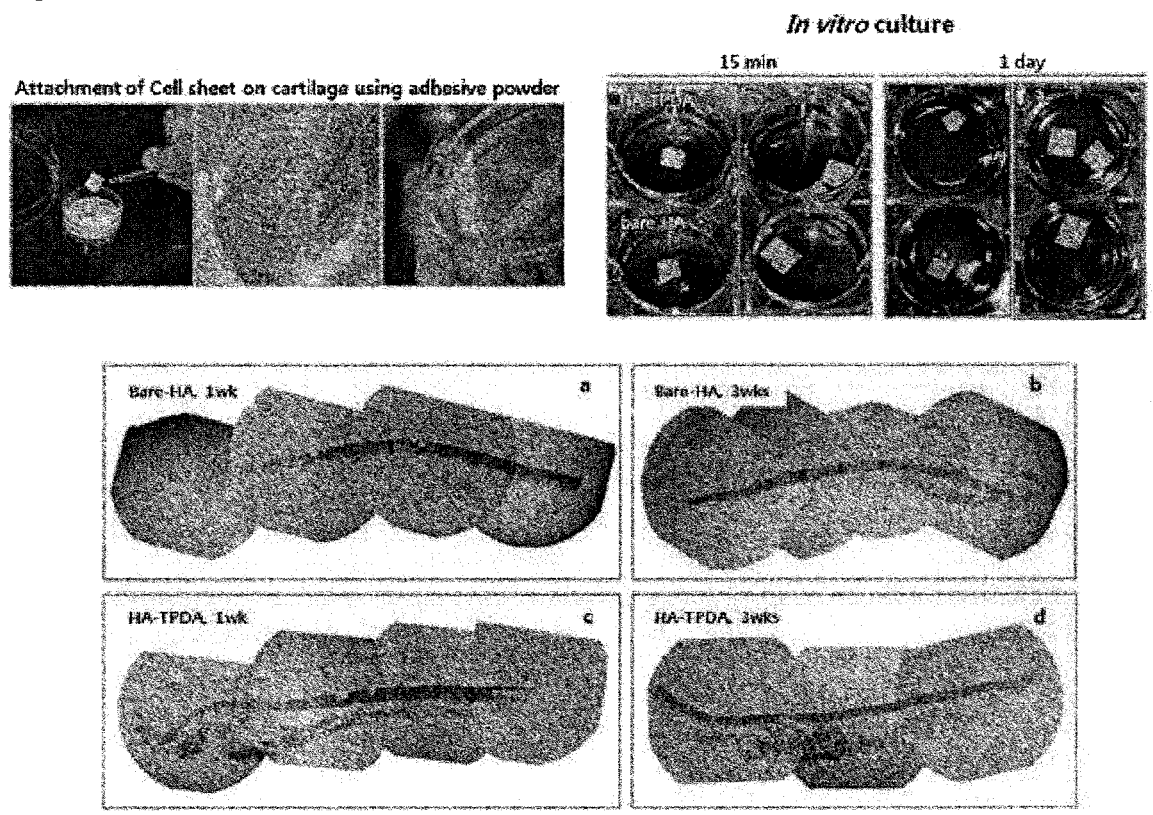
FIG. 4 is a picture showing a histological analysis of the remaining cell layers after adhesion of cells in the form of a sheet using HA-TPDA followed by cultivation for 1 week or 3 weeks, in order to confirm the adhesive effect of the surface-modified hydroxyapatite. Bare-HA represents a general hydroxyapatite-applied group, and HA-TPDA represents a HA-TPDA-applied group.

HA-TPDA powders were sprinkled on the cartilage tissues obtained from rabbit ears, and unbound HA-TPDA powders were brushed out. Multiple layers of bone marrow stromal cells (BMSCs) obtained from rats and cultured in the form of a sheet were attached to the tissues. The tissues were cultured in an alpha-MEM medium containing 20% fetal bovine serum, 1% penicillin/streptomycin, 2 mM L-glutamine, $10^{-8}$M dexamethasone and $10^{-4}$M ascorbic acid for 1 week to 3 weeks, and fixed with 4% paraformaldehyde in PBS. The fixed tissues were embedded in paraffin and cut. The degree of tissue adhered was determined by histological staining, and the results are shown in FIG. 4. As shown in FIG. 4, it was confirmed that the sheet form was remained for a longer time in the HA-TPDA-applied group than in a general hydroxyapatite-applied group.

Example 4

Figure 5:
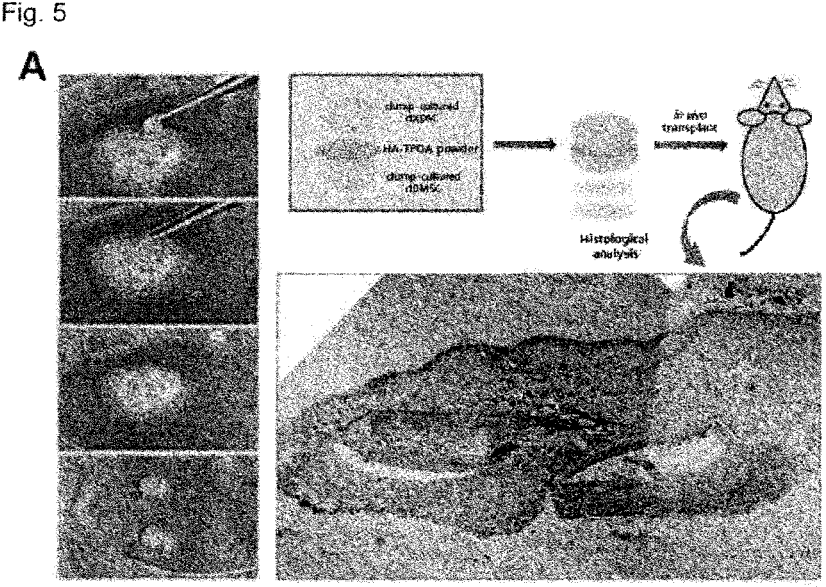
FIG. 5 is a picture showing a histological analysis of two kinds of clump-cultured cells after adhesion of the same using HA-TPDA and subcutaneous transplantation into a nude mouse followed by cultivation for 8 weeks, in order to confirm the adhesive effect of the surface-modified hydroxyapatite. A represents a schematic process of the experiment in which the two kinds of cells are xiphoid process-derived stromal cells (XDSCs) and bone marrow stromal cells (BMSCs). B is a histological picture in which the chondrogenic layer was generated from the xiphoid process-derived stromal cells, and the osteogenic layer was generated from the bone marrow stromal cells.
Figure 5:
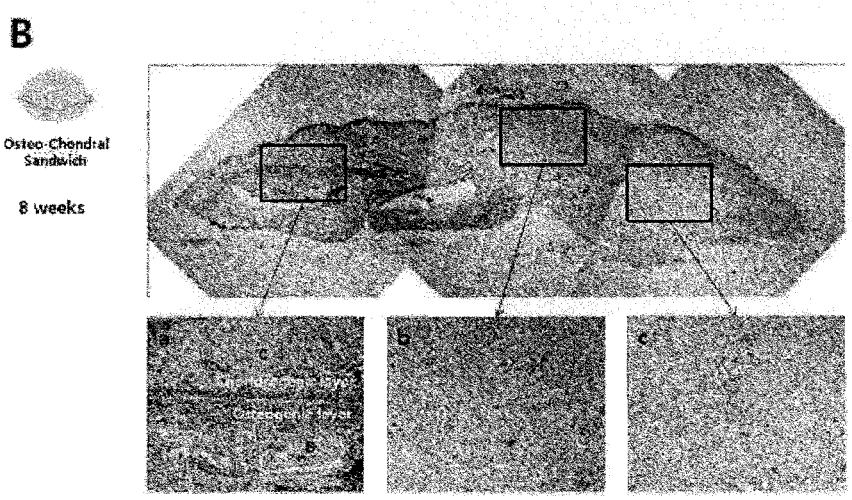

Nude Mouse Transplantation Experiment in Order to Confirm the Adhesive Ability of HA-TPDA Between Cell Clumps Cells isolated from rat xiphoid process cartilage (rtXD-SCs) and cells isolated from rat bone marrow (rtBMSCs) were each cultured in clump form in an alpha-MEM medium containing 20% fetal bovine serum, 1% penicillin/streptomycin, 2 mM L-glutamine, $10^{-8}$M dexamethasone and $10^{-4}$M ascorbic acid, and HA-TPDA was applied to the boundary surface so that the two cell clumps bound to each other. Such bound cell clumps were subcutaneously transplanted into a nude mouse. After 8 weeks, the transplanted tissues were isolated and fixed with 4% paraformaldehyde in PBS. The fixed tissues were embedded in paraffin and cut. The degree of tissue adhered was determined by histological staining, the results of which are shown in FIG. 5. As shown in FIG. 5B, it was confirmed that the chondrogenic layer was generated from the xiphoid process-derived stromal cells, and the osteogenic layer was generated from the bone marrow stromal cells, and the two kinds of cell clumps intimately bound to each other.

Example 5

Nude Mouse Transplantation Experiment in Order to Confirm the Adhesive Ability of HA-TPDA between a Cell Clump and a Piece of Ectopic Bone Cells isolated from rat bone marrow were cultured in an alpha-MEM medium containing 20% fetal bovine serum, 1% penicillin/streptomycin, 2 mM L-glutamine, $10^{-8}$M dexamethasone and $10^{-4}$M ascorbic acid. $2 \times 10^6$ cells were cultured with 40 mg HA/TCP for 1 hour so that the cells bound to the surface of HA/TCP. Such cultured cells and HA/TCP were subcutaneously transplanted into a nude mouse and maintained for 15 weeks or more, allowing the formation of ectopic bone.

Figure 6:
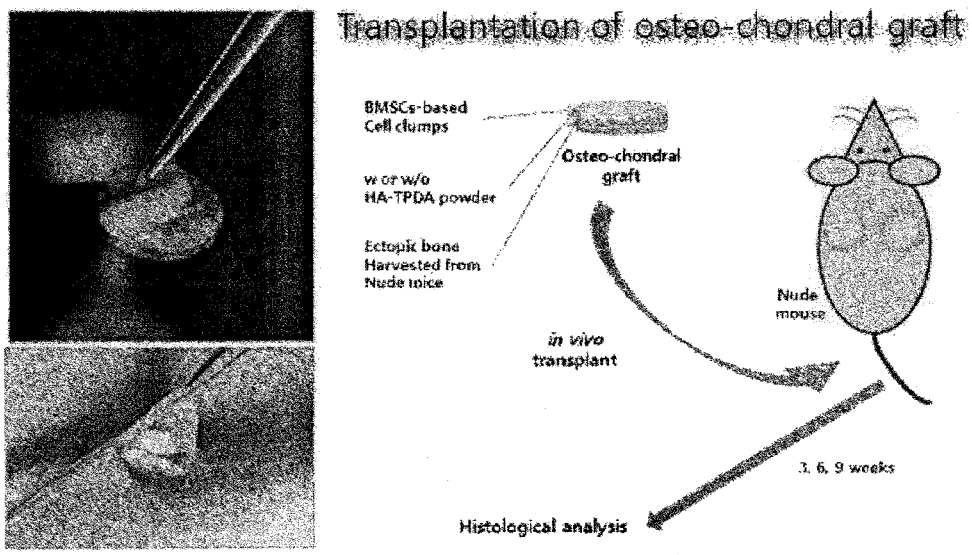
FIG. 6 is a schematic view showing an experimental process of attaching clump-cultured bone marrow stromal cells (BMSCs) onto the surface of a piece of ectopic bone harvested from a transplanted nude mouse and subcutaneously transplanting the piece into a nude mouse, in order to confirm the adhesive effect of the surface-modified hydroxyapatite.
Figure 7:
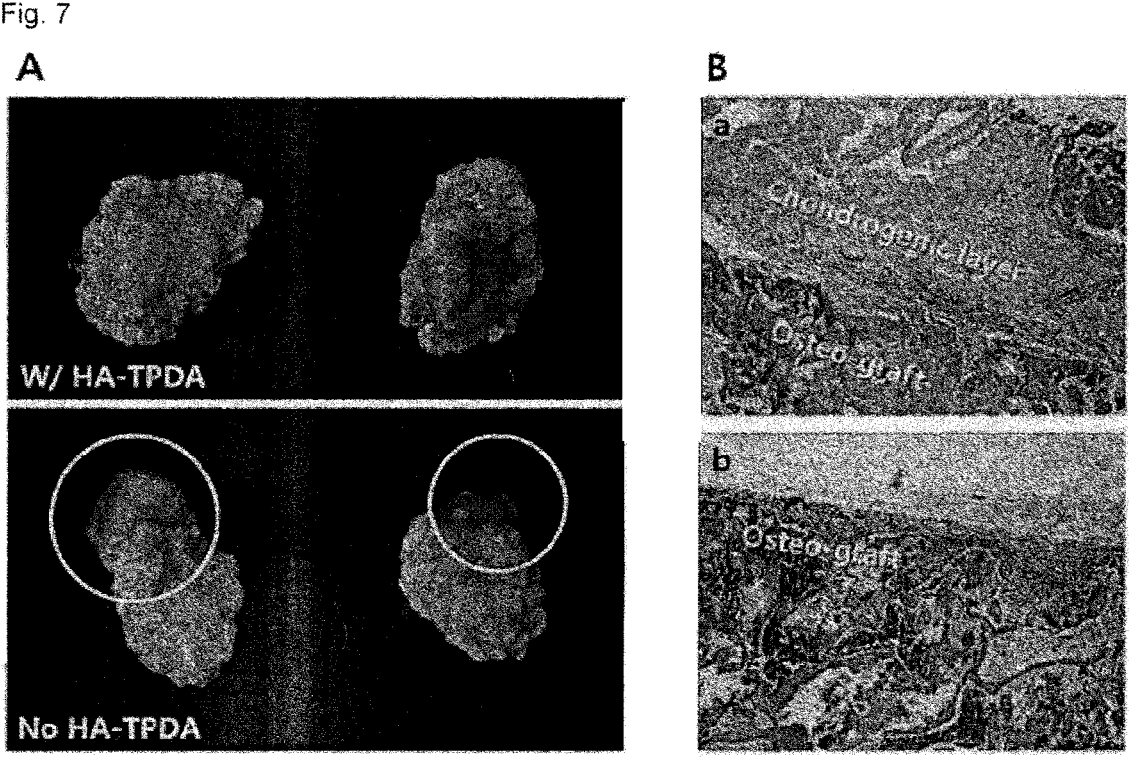
FIG. 7 is a picture showing the implant isolated from the nude mouse 3 weeks after transplantation according to the method of FIG. 6 (A is a naked-eye picture, and B is the histological staining result).

As shown in FIG. 6, a piece of the formed ectopic bone was collected, and its surface was scraped with a surgical knife so that bone tissues were revealed. Cell clump derived from rat bone marrow stromal cells (rtBMSCs) was applied onto the surface of the piece of ectopic bone using HA-TPDA for adhesion. The adhered tissues were again subcutaneously transplanted into a nude mouse. After 3 weeks, the implant was collected and fixed with 4% paraformaldehyde in PBS. The fixed tissues were de-calcified with 0.25M EDTA for 3 weeks, and then embedded in paraffin and cut. The degree of tissue adhered was determined by histological staining, the results of which are shown in FIG. 7. As shown in FIG. 7, it was confirmed that in the control group the cell clump derived from BMSCs did not bind to the surface of the piece of bone but was slid to the side, whereas in the HA-TPDA-applied group the adhered form was well maintained and the adhered surface was intimately formed.

Example 6

Confirmation of the Adhesive Effect of HA-TPDA Between Cartilage and Bone Using the Rabbit Autologous Chondrocyte Transplantation (ACT) Model After anesthetizing a rabbit, the abdomen was sterilized with povidone and alcohol, cut to collect xiphoid process and stitched up. Connective tissues on the surface of the collected xiphoid process were thoroughly torn off using a surgical knife, cut into small pieces and treated with 0.5% collagenase II overnight to obtain xiphoid process-derived stromal cells (XDSCs). The cells were cultured in high concentrations in an alpha-MEM medium containing 20% fetal bovine serum, 1% penicillin/streptomycin, 2 mM L-glutamine, $10^{-8}$M dexamethasone and $10^{-4}$M ascorbic acid to be in clump form.

Figure 8:
FIG. 8 is a picture showing transplantation of chondrocytes (cartilage cells) into a rabbit articular cartilage damage model using HA-TPDA, in order to confirm the adhesive effect of the surface-modified hydroxyapatite.
Figure 8:
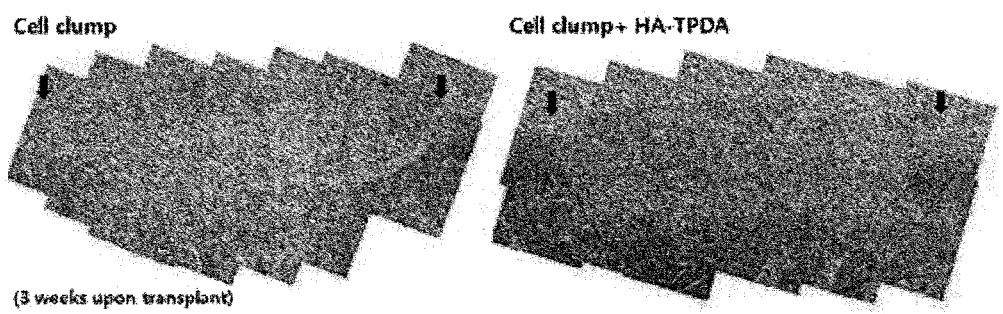

As shown in FIG. 8, after anesthetizing the rabbit, the skin of the knee joint was incised on the side so that the cartilage of the articular surface was revealed. The range of cartilage damage was marked with a 5-mm biopsy punch, and a full-thickness wound was made using a dental drill so that subchondral bone was revealed. The surface of the formed wound was thoroughly wiped out with sterile gauze, and a thin layer of HA-TPDA was sprinkled thereon. HA-TPDA that failed to bind to the surface of the subchondral bone was carefully blown off using a spoid. HA-TPDA was covered with the autologous cell-derived XDSCs cultured in clump form to ensure a binding. The wound was then stitched up in the order of the articular capsule, hypoderma and skin.

Figure 9:
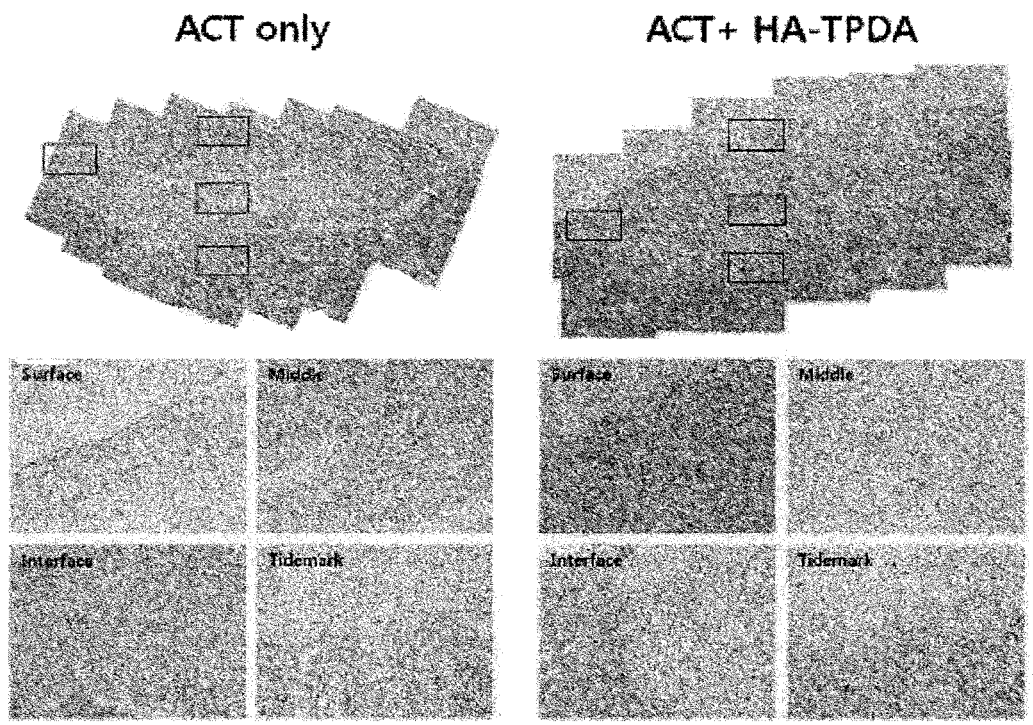
FIG. 9 is a picture showing the histological staining result of the implant isolated from the rabbit 3 weeks after transplantation according to the method of FIG. 8 (pale pink color: cartilage tissues, bold pink color: bone tissues).

After 3 weeks, the rabbit was euthanized, and the surgery region was incised. Bone in the transplanted region was cut with a saw, collected and fixed with 4% paraformaldehyde in PBS. The fixed tissues were decalcified with 0.25M EDTA for 3 weeks, and then embedded in paraffin and cut. The degree of adhesion between bone and cartilage was determined by histological staining, the results of which are shown in FIG. 9. As shown in FIG. 9, it was confirmed that in the control group the implant did not make an intimate bonding with the cartilage-damage region, whereas in the HA-TPDA-applied group the implant was adhered to the damaged region with excellent affinity showing nice gradation of calcification, which helps integration of implant to the natural tissue.

The invention claimed is:
1. A method of adhesion between bone and cartilage, comprising:
applying a composition comprising a surface-modified hydroxyapatite as an active ingredient to provide adhesion between said bone and cartilage, with the proviso that the composition does not include chitosan,
wherein the surface-modified hydroxyapatite is modified such that there is an aldehyde group on the surface of the surface-modified hydroxyapatite and
wherein the hydroxyapatite is of the formula $M_{10}Z_6X_2$ wherein M is $Ca^{2+}$, Z is $PO_4^{3-}$, and X is $OH^-$.
2. The method of claim 1, wherein the surface-modified hydroxyapatite is in the form of a powder.

* * * * *